United States Patent
Hong et al.

(10) Patent No.: US 6,635,270 B2
(45) Date of Patent: Oct. 21, 2003

(54) NMDA RECEPTOR AGONIST PHARMACEUTICAL COMPOSITIONS

(75) Inventors: Jinyang Hong, Stonington, CT (US); Yesook Kim, Branford, CT (US)

(73) Assignee: Pfizer Inc, New York, NY (US)

( * ) Notice: Subject to any disclaimer, the term of this patent is extended or adjusted under 35 U.S.C. 154(b) by 100 days.

(21) Appl. No.: 10/010,827

(22) Filed: Dec. 5, 2001

(65) Prior Publication Data

US 2002/0111366 A1 Aug. 15, 2002

Related U.S. Application Data

(60) Provisional application No. 60/255,372, filed on Dec. 13, 2000.

(51) Int. Cl.[7] ................................................. A61F 2/02
(52) U.S. Cl. ...................................................... 424/423
(58) Field of Search ......................................... 424/423

(56) References Cited

U.S. PATENT DOCUMENTS 5,272,160 A    12/1993   Chenard ...................... 514/327
5,710,168 A    1/1998    Chenard ...................... 514/327
6,008,233 A  * 12/1999   Andino et al. .............. 514/327

* cited by examiner

*Primary Examiner*—Carlos A. Azpuru
(74) *Attorney, Agent, or Firm*—Peter C. Richardson; Paul H. Ginsburg; Gabriel L. Kleiman

(57) ABSTRACT

This invention relates to stable pharmaceutical compositions of the NMDA receptor agonist, (1S,2S)-1-(4-hydroxyphenyl)-2-(4-hydroxy-4-phenylpiperidin-1-yl)-1-propanol], methods of preparing such pharmaceutical compositions and methods of treating stroke, spinal cord trauma, traumatic brain injury, multiinfarct dementia, CNS degenerative diseases such as Alzheimer's disease, senile dementia of the Alzheimer's type, Huntington's disease, Parkinson's disease, epilepsy, amyotrophic lateral sclerosis, pain, AIDS dementia, psychotic conditions, drug addictions, migraine, hypoglycemia, anxiolytic conditions, urinary incontinence and an ischemic event arising from CNS surgery, open heart surgery or any procedure during which the function of the cardiovascular system is compromised using the pharmaceutical compositions.

23 Claims, No Drawings

NMDA RECEPTOR AGONIST PHARMACEUTICAL COMPOSITIONS

This application is filed claiming priority from Provisional Application No. 60/255,372 filed Dec. 13, 2000.

BACKGROUND OF THE INVENTION

This invention provides stable pharmaceutical compositions of the N-methyl-D-aspartic acid (NMDA) receptor antagonist, (1S,2S)-1-(4-hydroxyphenyl)-2-(4-hydroxy-4-phenylpiperidin-1-yl)-1-propanol, methods of preparing such pharmaceutical compositions and methods of treating stroke, spinal cord trauma, traumatic brain injury, multiinfarct dementia, CNS degenerative diseases such as Alzheimer's disease, senile dementia of the Alzheimer's type, Huntington's disease, Parkinson's disease, epilepsy, amyotrophic lateral sclerosis, pain, AIDS dementia, psychotic conditions, drug addictions, migraine, hypoglycemia, anxiolytic conditions, urinary incontinence and an ischemic event arising from CNS surgery, open heart surgery or any procedure during which the function of the cardiovascular system is compromised, using the pharmaceutical compositions of this invention.

(1S,2S)-1-(4-Hydroxyphenyl)-2-(4-hydroxy-4-phenylpiperidin-1-yl)-1-propanol (hereafter referred to as the "Compound") is a neuroprotecting agent that is useful for the treatment of stroke, spinal cord trauma, traumatic brain injury, multiinfarct dementia, CNS degenerative diseases such as Alzheimer's disease, senile dementia of the Alzheimer's type, Huntington's disease, Parkinson's disease, epilepsy, amyotrophic lateral sclerosis, pain, AIDS dementia, psychotic conditions, drug addictions, migraine, hypoglycemia, anxiolytic conditions, urinary incontinence and an ischemic event arising from CNS surgery, open heart surgery or any procedure during which the function of the cardiovascular system is compromised. The Compound exhibits activity as an NMDA receptor antagonist. NMDA is an excitatory amino acid involved in excitatory neurotransmission in the central nervous system. NMDA antagonists are compounds that block the NMDA receptor by interacting with the receptor's binding site.

Antagonists of neurotransmission at NMDA receptors are useful therapeutic agents for the treatment of neurological disorders. U.S. Pat. No. 4,902,695 is directed to series of competitive NMDA antagonists useful for the treatment of neurological disorders, including epilepsy, stroke, anxiety, cerebral ischemia, muscular spasms, and neurodegenerative disorders such as Alzheimer's disease and Huntington's disease. U.S. Pat. No. 4,968,878 is directed to a second series of competitive NMDA receptor antagonists useful for the treatment of similar neurological disorders and neurodegenerative disorders. U.S. Pat. No. 5,192,751 discloses a method of treating urinary incontinence in a mammal, which comprises administering an effective amount of a competitive NMDA antagonist.

Commonly assigned U.S. Pat. No. 5,272,160 and commonly assigned U.S. Pat. No. 5,710,168 (the disclosures of which are hereby incorporated by reference) disclose the Compound and methods of using the Compound for treatment of diseases or conditions that are susceptible to treatment by blocking NMDA receptor sites, including stroke, spinal cord trauma, traumatic brain injury, multiinfarct dementia, CNS degenerative diseases, epilepsy, amyotrophic lateral sclerosis, pain, AIDS dementia, psychotic conditions, drug addictions, migraine, hypoglycemia, anxiolytic conditions, urinary incontinence and ischemic events.

Commonly assigned U.S. Pat. No. 6,008,233 (the disclosure of which is hereby incorporated by reference) discloses the methanesulfonate trihydrate of the Compound and uses thereof for treatment of the aforesaid diseases and conditions.

The Compound is preferably administered as an intravenous infusion lasting many hours. Such administration is intended to maintain a desired blood level of the compound for the duration of the therapy. Typically, therapy with the Compound is initiated in the hospital emergency room and continues for a desired time in the ICU or other critical care units.

Formulations and dosage presentations of the Compound should be designed for convenient and efficient administration and should be especially suited for the emergency setting. Degradation of the Compound in such formulations should be minimized.

SUMMARY OF THE INVENTION

This invention provides relatively stable formulations of the Compound in aqueous solutions made by reducing or removing the presence of trace metal ions in the solutions. Stability is further improved through the use of a pharmaceutically acceptable buffer. Additional stability is afforded by reducing the presence of oxygen in the formulations.

One aspect of the present invention is pharmaceutical compositions comprising a pharmaceutically effective amount of (1S,2S)-1-(4-hydroxyphenyl)-2-(4-hydroxy-4-phenylpiperidin-1-yl)-1-propanol or a pharmaceutically acceptable salt thereof and water, wherein said compositions contain less than about 2 parts per million of free copper ion and less than about 2 parts per million of free iron ion.

Another aspect of the present invention is pharmaceutical compositions comprising (1S,2S)-1-(4-hydroxyphenyl)-2-(4-hydroxy-4-phenylpiperidin-1-yl)-1-propanol or a pharmaceutically acceptable salt thereof, water and a pharmaceutically acceptable chelating agent, preferably ethylenediaminetetraacetic acid, citric acid, succinic acid or tartric acid or a pharmaceutically acceptable salt thereof, at a concentration effective to chelate with trace metal ions present in said composition.

A further aspect of the present invention is pharmaceutical compositions comprising (1S,2S)-1-(4-hydroxyphenyl)-2-(4-hydroxy-4-phenylpiperidin-1-yl)-1-propanol or a pharmaceutically acceptable salt thereof in an aqueous solution, wherein the percent of the degradation product, 4-hydroxybenzaldehyde, is no more than about 0.15 percent of said composition following storage at 50° C. for 12 weeks, preferably no more than about 0.07 percent and most preferably no more than about 0.04 percent.

An additional aspect of this invention is pharmaceutical compositions comprising (1S,2S)-1-(4-hydroxyphenyl)-2-(4-hydroxy-4-phenylpiperidin-1-yl)-1-propanol or a pharmaceutically acceptable salt thereof in an aqueous solution, wherein the percent of the degradation product, 4-hydroxy-4-phenylpiperidine, is no more than about 0.2 percent of said composition following storage at 50° C. for 12 weeks, preferably no more than about 0.1 percent and most preferably no more than about 0.05 percent.

An additional aspect of this invention is methods of treating stroke, spinal cord trauma, traumatic brain injury, multiinfarct dementia, CNS degenerative diseases such as Alzheimer's disease, senile dementia of the Alzheimer's type, Huntington's disease, Parkinson's disease, epilepsy, amyotrophic lateral sclerosis, pain, AIDS dementia, psychotic conditions, drug addictions, migraine, hypoglycemia, anxiolytic conditions, urinary incontinence and an ischemic event arising from CNS surgery, open heart surgery or any procedure during which the function of the cardiovascular system is compromised, in mammals, comprising administering to a mammal in need of such treatment a pharmaceutical composition of this invention.

In a preferred embodiment of the composition aspects of this invention, the compositions are substantially free of free copper ion and free iron ion.

In another preferred embodiment of the composition aspects of this invention, the compositions contains less than about 2 parts per million of any free trace metal ion, and more preferably is substantially free of any free trace metal ion.

Another preferred embodiment of the composition aspects of this invention provides that the compositions comprise a pharmaceutically acceptable buffer at a concentration effective to maintain the pH of the compositions at between about 3.8 to about 5.0 and more preferably at between about 4.0 to about 4.5. In a more preferred embodiment, the anion of the buffer is selected from acetate, citrate, tartrate, formate and lactate, most preferably lactate.

A further preferred embodiment of the composition aspects of this invention provides that the compositions are substantially free of oxygen.

In a preferred embodiment of the method of treatment aspects of this invention, the mammal is a human.

The term "chelating agent" as used herein means any compound that sequesters, forms a complex or otherwise interacts with trace metal ions such that the destabilizing effect of such metal ions to the Compound in aqueous solution is minimized. Exemplary chelating agents include ethylenediaminetetra-acedic acid (EDTA) and its salts, trans-1,2-diaminocyclohexanetetra-acedic acid (DCTA) and its salts, bis-(2-aminoethyl)ethyleneglycol-NNN'N'-tetraacetic acid (EGTA) and its salts, diethyllenetriamineepenta-acetic acid (DTPA) and its salts, tri-(2-aminoethyl)amine (tren), NNN'N'-tetra-(2-aminoethyl)ethylenediamine (penten), nitrilotriacedic acid (NTA) and its salts, 2,3-dimercapto-1-propanesulfonic acid (DMPS) and its salts, meso-2,3-dimercaptosuccinnic acid (DMSA) and its salts, hydroxyl acids such as citric, tartaric, lactic, succinic, etc. and their salts, and certain amino acids such as glycine, histidine, and glutamic acid and their salts.

The term "Degradant 1" as used herein refers to the degradation product of the Compound, 4-hydroxybenzaldehyde.

The term "Degradant 2" as used herein refers to the degradation product of the Compound, 4-hydroxy-4-phenylpiperidine.

The terms "free copper ion", "free iron ion" and "free trace metal ion" as used herein means copper ions, iron ions or trace metal ions, respectively, that when present in an aqueous composition comprising the Compound are in a form or state as to enable them to cause, initiate, encourage or catalyze degradation of the Compound.

"Headspace" refers to the difference in volume between a closed container (e.g., a vial) and the volume of liquid contained in that container. The headspace can be quantified as a percent of the total volume of the closed container.

The expression "means to remove trace metal ions" as used herein means any means that may be used to remove trace metal ions from an aqueous solution. For example, such means can include the use of metal chelating resins or other chelating reagents that are known to those skilled in the art.

The term "non-reactive gas" as used herein means any gas that does not react or interact chemically with a pharmaceutical composition or any of its components. Such gas is preferably nitrogen, but may be argon, helium, or any other gas known by those skilled in the art for its non-reactive properties.

The expressions "percent of Degradant 1" and "percent of Degradant 2" means the percent of the applicable degradation product present in a pharmaceutical composition of the Compound in weight versus weight (w/w) terms. The percent is calculated from peak areas derived from HPLC analysis according to the formula:

$$\text{Percent of Degradant} = [(A_{SAMP} \times D_{SAMP})/(R_{AVG} \times C_{LAB})] \times 100$$

where:

$A_{SAMP}$=impurity peak area $D_{SAMP}$=dilution factor, calculated as:

$$D_{SAMP} = C_{LAB}/C_{SAMP}$$

where:

$C_{LAB}$=label concentration of the Compound in the formulation being tested (free base concentration)

$C_{SAMP}$=concentration of the free base of the Compound in the sample tested (based upon dilution of the label concentration used to make the sample)

$R_{AVG}$=is the average standard response factor ("R") obtained from analysis of a standard solution, calculated as:

$$R = A_{STD}/(C_{STD} \times PF)$$

where:

$A_{STD}$=peak area of the Compound in the standard solution $C_{STD}$=concentration of the Compound in the standard solution PF=potency factor of the Compound in the standard solution, calculated as the molar weight of the free base of the compound divided by the molar weight of the actual compound in the standard solution.

The dilution factor, $D_{SAMP}$, accounts for dilution that may be necessary so that the sample tested is within the validated concentration limits of the HPLC method.

The expression "pharmaceutically acceptable" as used herein refers to carriers, diluents, excipients, buffers and/or salts that are compatible with the other ingredients of the formulation and are not deleterious to the recipient thereof.

The term "substantially free" as used herein with respect to the presence of trace metal ions in pharmaceutical compositions comprising the Compound, means a quantity that is less than that which would have a substantial effect on degradation of the Compound in such compositions. Notwithstanding the foregoing, such an amount is less than about 2 ppm for any applicable trace metal ion. The term "substantially free" as used herein with respect to the presence of oxygen in or in contact with pharmaceutical compositions comprising the Compound, means a quantity of oxygen that is less than that which would have a substantial effect on degradation of the Compound in such compositions. For example, in compositions packaged in closed containers or vials having a headspace wherein such headspace is 25% or less of the volume of the container or vial, the term "substantially free" means that there is less than 10% oxygen in such headspace.

The term "trace metal ion" as used herein means any metal ion that, when present in an aqueous pharmaceutical composition comprising the Compound, causes, initiates, encourages or catalyzes degradation of the Compound, especially ions of transition metals and most especially iron and copper ions.

DETAILED DESCRIPTION OF THE INVENTION

The active ingredient in the present pharmaceutical compositions is (1S,2S)-1-(4-hydroxyphenyl)-2-(4-hydroxy-4-phenylpiperidin-1-yl)-1-propanol, which may be present as its free base or as a pharmaceutically acceptable salt, preferably the methanesulfonate (mesylate) salt. The preparation of (1S,2S)-1-(4-hydroxyphenyl)-2-(4-hydroxy-4-phenylpiperidin-1-yl)-1-propanol is described in U.S. Pat. No. 5,272,160 and in U.S. Pat. No. 6,008,233. The preparation of the mesylate salt trihydrate is described in U.S. Pat. No. 6,008,233.

In a representative example, (1S,2S)-1-(4-hydroxyphenyl)-2-(4-hydroxy-4-phenylpiperidin-1-yl)-1-propanol is administered to a stroke or head trauma patient at the emergency site or in the hospital emergency room by intravenous infusion. Therapy would continue in the ICU or other critical care units. The amount of the compound to be administered would, in part, depend on the body weight of the patient.

A concentrated solution of (1S,2S)-1-(4-hydroxyphenyl)-2-(4-hydroxy-4-phenylpiperidin-1-yl)-1-propanol that can readily be diluted according to the needs of the patient provides the required dosing flexibility. The concentrated solution would, if necessary, be diluted to the appropriate concentration for administration to the patient.

Formulations of the present pharmaceutical compositions may be in the form of concentrated solutions intended to be diluted in a suitable IV diluent prior to administration. The formulations may also be prepared as ready to use forms that are at concentrations that can be administered without further dilution. The preferred concentration of the compositions in concentrate form is 10 milligrams of the free base of the active compound, (1S,2S)-1-(4-hydroxyphenyl)-2-(4-hydroxy-4-phenylpiperidin-1-yl)-1-propanol, per 1 milliliter of solution (i.e., 10 mgA/mL). The preferred concentration of the ready to use forms is 1.25 mgA/mL.

The composition is administered full strength or is diluted as required. A preferred dosage concentration for administration to the patient is 0.1 mgA/mL to 10 mgA/mL. A more preferred dosage for administration is at a concentration of 0.5 mgA/mL to 2.0 mgA/mL. An even more preferred dosage concentration is 1.25 mgA/mL. The preferred IV diluent of the composition is normal saline solution (0.9% NaCl).

Two degradants produced by the chemical degradation of (1S,2S)-1-(4-hydroxyphenyl)-2-(4-hydroxy-4-phenylpiperidin-1-yl)-1-propanol in aqueous solutions are the compounds 4-hydroxybenzaldehyde (hereafter "Degradant 1") and 4-hydroxy-4-phenylpiperidine (hereafter "Degradant 2"). While not essential to the practice of this invention and not intending to be limited in any manner thereby, it is believed that such degradation is the result of oxidation of (1S,2S)-1-(4-hydroxyphenyl)-2-(4-hydroxy-4-phenylpiperidin-1-yl)-1-propanol.

Trace metal ion contamination has been found to be a critical factor in the degradation of the Compound. Such effects are exemplified by spiking experiments of solutions containing the Compound with iron or copper ions. Table 1 shows the effect of iron and copper ions in unbuffered water for injection (WFI) solution on degradation product formation.

TABLE 1

Effect of $Fe^{2+}$ and $Cu^+$ spiking on degradation of the Compound. Numbers represent percent of Degradant 1 (w/w).

| Days at 70° C. | WFI only | $Fe^{2+}$ (20 ppm) | $Cu^+$ (20 ppm) |
|---|---|---|---|
| Day 0 | 0.002% | 0.024% | 0.085% |
| Day 3 | 0.007% | 0.061% | 0.107% |
| Day 7 | 0.009% | 0.110% | 0.128% |

WFI= water for injection. Chelex ® treated solutions containing 1.25 mgA/ml of the Compound were spiked with 20 ppm of iron or copper and then autoclaved at 121° C. for 8 minutes.

An effective means of improving the chemical stability of the Compound is achieved by removing trace metal ions from the aqueous formulation. One method of metal ion removal is by employing agents specifically designed for this purpose. Exemplary metal ion removing agents include chelating resins such as Chelex® (Chelex is a trademark of Bio-Rad Laboratories, Inc., Hercules, Calif.). However, other pharmaceutically acceptable chelating resins or reagents performing the same function would be acceptable so long as they do not detrimentally affect the Compound or other components of the formulation.

Treatment for removal of trace metal ions may be performed on individual components of the formulation prior to final formulation or such treatment may be performed on the formulation itself. For example, water that is to be used in the formulation may be treated to remove trace metals. Alternatively, concentrated buffer solutions may be treated prior to dilution with water and formulation with the active ingredient. In another alternative, the aqueous solution containing all components of the formulation except for the active pharmaceutical ingredient may be treated to remove metal ions. A still further alternative is to treat the complete formulation that contains all components, including the active ingredient.

An alternative to removal of trace metal ions is to incorporate certain compounds in the formulation that will form a chelate with the trace metal ions, thereby minimizing their degradation effect. Examples of such chelating agents include ethylenediaminetetraacetic acid (EDTA) disodium and citrate and tartrate buffers. The preferred concentration of EDTA disodium, citrate buffer and tartrate buffer is 10 mM each. Citrate and tartrate are believed to act as chelating agents for trace metal ions. In addition, succinate is believed to act as a chelating agent. Other chelating agents will be apparent to those skilled in the art in light of this disclosure.

Aqueous solutions of the Compound are susceptible to pH shift. The compound is believed to exhibit its best chemical stability between pH 4.0 and 4.5. When the Compound is formulated with only water, the pH of the formulation increases above 5. This pH shift results in conditions favorable to the oxidative degradation reaction, thus accelerating the degradation of the aqueous formulation. The increase in pH also decreases the solubility of the compound, thereby increasing the possibility of precipitation out of solution.

The pH shift may be minimized by using a suitable buffer. Those skilled in the art will appreciate that any pharmaceutically acceptable buffer that maintains the pH of the formulation within a certain range may be used. The pH range of such buffer is preferably between about 3.8 and about 5.0, and most preferably between 4.0 and 4.5. Suitable buffers include, but are not limited to, acetate, benzoate, citrate, formate, lactate and tartrate buffers, preferably lactate.

Table 2 exemplifies the use of various buffers to stabilize the pH of formulations containing 10 mgA/ml of the Compound.

TABLE 2

| | pH at 70° C. | | | | |
|---|---|---|---|---|---|
| Buffer lot | Initial (post-TS) | 2 days | 4 days | 7 days | 21 days |
| 10 mM acetate | 4.16 | N/T | 4.14 | 4.14 | 4.17 |
| 10 mM benzoate | 4.21 | N/T | 4.16 | 4.20 | N/A |
| 10 mM citrate | 4.16 | 4.16 | N/T | 4.17 | 4.11 |
| 10 mM formate | 4.17 | 4.18 | N/T | 4.16 | 4.13 |
| 3 mM lactate | 4.24 | 4.21 | N/T | 4.20 | 4.14 |
| 10 mM tartrate | 4.15 | 4.17 | N/T | 4.17 | 4.07 |

N/T = not taken
N/A = not available
TS = terminal sterilization

In order to further improve stability of the active compound, it is preferable that the oxygen content in the formulation be reduced. This can be done by sparging the formulation solution with nitrogen, argon or other non-reactive gas and, when the compositions of the invention are packaged in vials or similar containers containing a headspace, using such inert gas for the headspace. When the compositions of the invention are packaged so that they contain a headspace, it is preferable that the oxygen content in the headspace be less than about 12% and most preferably less than about 8%. Oxygen may be removed by other methods, including the use of a vacuum to remove air and oxygen. Other methods of oxygen removal will be apparent to those skilled in the art.

A preferred presentation of the composition aspects of the invention comprises the Compound at a concentration of 10 mgA/mL. This concentration is near the maximum solubility of the Compound (about 12 mgA/mL at 5° C.). The preferred solution of the composition is 10 mM lactate buffer. However, those skilled in the art will appreciate that buffer solutions of other anions may be used, including, but not limited to, buffer solutions of the anions acetate, citrate, tartrate and formate.

A preferred packaging of the compositions is a 40 cc, Flint Type I molded glass vial with rubber stopper and aluminum shell. Alternative presentations can include other vial or container types, pre-filled syringes or pre-filled IV bags. Other packaging presentations will be apparent to those skilled in the art.

Vials are preferably sterilized by terminal sterilization methods employing an autoclave. Preferably, sterilization is for 8 minutes at 121° C. Sterilization may cause a slight shift of pH. In the lactate buffered formulation, pH shifted slightly down. In order to achieve a mid-point in the preferred pH range, the initial pH is preferably set to 4.5. The terminal sterilization cycle reduces the pH to about 4.2.

EXPERIMENTAL EXAMPLES

The present invention is illustrated by the following examples, but is not limited to the details thereof.

Percentages of Degradant 1 and Degradant 2 where measured using reverse-phase HPLC analysis on a Kromasil® C4 column, 5 μm, 25 cm length×4.6 mm ID (EKA Chemicals, Bohus Sweden). Column temperature was 30° C.±5° C. Mobile phase A: water/acetonitrile/trifluoroacetic acid, 90/10/0.1 (v/v/v). Mobile phase B: water/acetonitrile/trifluoroacetic acid, 40/60/0.1 (v/v/v). Gradient profile: linear. Detection: UV @ 215nm. Flow rate: 1.5 mL/min. Injection volume: 10 μL.

Example 1

Effect of Treatment with a Chelating Resin

Solutions of sodium chloride of 0.3, 0.6 and 0.9% were treated with 5% w/w of Chelex® resin and stirred slowly for 1 hour. The pH of the solutions was adjusted to 4.6 while stirring with the Chelex resin. The mixture was then filtered. Control samples of sodium chloride solutions of 0.3, 0.6 and 0.9% were prepared which were not treated with the Chelex resin. Treated and untreated solutions were combined with (1S,2S)-1-(4-hydroxyphenyl)-2-(4-hydroxy-4-phenylpiperidin-1-yl)-1-propanol at a concentration of 1.25 mgA/ml and stored in sealed 5 cc Flint type I molded vials containing 4.0 ml solution fill and 2.0 ml air headspace at 70° C. for 7 days. The results of this experiment are represented in Table 3.

TABLE 3

| Numbers represent percent of Degradant 1 (w/w). | | |
|---|---|---|
| % NaCl | Untreated | Treated |
| 0.3 | 0.034% | 0.004% |
| 0.6 | 0.038% | 0.003% |
| 0.9 | 0.033% | 0.003% |

Example 2

Effect of Formulating with a Chelating Agent

The following solutions were made to a concentration of 10 mM each at pH 4.2:

1. Unbuffered normal saline (0.9% NaCl);
2. 10 mM Citrate buffer in normal saline (0.9% NaCl);
3. 10 mM Tartrate buffer in normal saline (0.9% NaCl); and
4. 10 mM EDTA disodium in normal saline (0.9% NaCl);

Solutions of each were combined with (1S,2S)-1-(4-hydroxyphenyl)-2-(4-hydroxy-4-phenylpiperidin-1-yl)-1-propanol to a concentration of 1.25 mgA/ml and the pH was adjusted to 4.2. Each formulation was subjected to an 8 minute autoclave cycle at 121° C. and then stored at 70° C. The results of this experiment are represented in Table 4 below.

TABLE 4

| Numbers represent percent of Degradant 1 w/w). | | | | |
|---|---|---|---|---|
| | 0.9% NaCl Saline | 10 mM Tartrate | 10 mM Citrate | 10 mM EDTA |
| Day 0 | N/A | 0.002% | 0.000% | 0.000% |
| Day 3 | N/A | 0.003% | 0.001% | 0.000% |
| Day 7 | 0.033% | 0.006% | 0.001% | 0.002% |

N/A= not available

Example 3

4-Hydroxybenzaldehyde (Degradant 1)

NMR analysis was performed at ambient temperature on a Bruker Avance DRX 500 MHz NMR spectrometer using a Bruker 5 mm gradient broadband inverse probe (Bruker Instruments, Inc., Billerica, Mass.). Sample was dissolved in 99.9% deuterated dimethyl sulfoxide (DMSO).

| $^{13}$C-NMR | | $^1$H-NMR | |
|---|---|---|---|
| Carbon (PPM) | H's Attached | Proton (PPM) δ | Proton Multiplicity |
| 115.84 | 1 | 6.92 | doublet |
| 128.43 | 0 | | |
| 132.10 | 1 | 7.74 | Doublet |
| 163.32 | 0 | | |
| 190.95 | 1 | 9.77 | Singlet |

Example 4

4-Hydroxy-4-phenylpiperidine (Degradant 2)

NMR analysis was performed at ambient temperature on a Bruker Avance DRX 500 MHz NMR spectrometer using a Bruker 5 mm gradient broadband inverse probe. Sample was dissolved in 99.9% deuterated dimethyl sulfoxide (DMSO).

| $^{13}$C-NMR | | $^1$H-NMR | |
|---|---|---|---|
| Carbon (PPM) | H's Attached | Proton (PPM) δ | Proton Multiplicity |
| 39.05 | 2 | 1.49 | doublet |
| | | 1.77 | triplet |
| 42.03 | 2 | 2.70 | doublet |
| | | 2.92 | triplet |
| 70.41 | 0 | | |
| 124.70 | 1 | 7.46 | doublet |
| 125.97 | 1 | 7.18 | triplet |
| 127.76 | 1 | 7.30 | triplet |
| 150.76 | 0 | | |

Example 5

Formulation of (1S,2S)-1-(4-hydroxyphenyl)-2-(4-hydroxy-4-phenylpiperidin-1-yl)-1-propanol in Lactate Buffer

| Component | Grade | Function | Weight (mg/vial) | Concentration (mg/ml) |
|---|---|---|---|---|
| (1S,2S)-1-(4-hydroxyphenyl)-2-(4-hydroxy-4-phenylpiperidin-1-yl)-1-propanol mesylate trihydrate | Pharm | Active ingredient | 586.01 | 14.577 (equal to 10 mgA/ml) |
| Lactic Acid | USP | Buffer | 41.12 | 1.023 |
| Sodium Hydroxide | NF | pH modifier | Ca 13.87 | Ca 0.345 |
| Hydrochloric Acid | NF | pH modifier | 0 | 0 |
| Water for Injection | USP | Vehicle | 39711.76 | 987.855 |

USP= United States Pharmacopoeia
NF= National Formulary

The pH of the initial formulation is set at pH 4.5 to accommodate the slight pH down-shifting upon terminal sterilization. The terminal sterilization cycle lowers the pH to about 4.2. Sodium hydroxide and hydrochloric acid are used as needed to adjust the solution to the desired pH.

Example 6

Accelerated Stability Study

A 10 mgA/ml solution of (1S,2S)-1-(4-hydroxyphenyl)-2-(4-hydroxy-4-phenylpiperidin-1-yl)-1-propanol in 10 mM lactate buffer was prepared. The pH of three separate portions was adjusted so that the initial post terminal sterilization pH was 3.9, 4.2 or 4.6. The formulation was packaged in vials containing varying concentrations of oxygen or in air. Terminal sterilization was by autoclave at 121° C. for 8 minutes. Samples were stored in 40 ml Flint type I vials with 40 ml fill and 10 ml headspace for 12 weeks at 30° C., 40° C. and 50° C.

The results of this experiment are presented in Table 5 and Table 6 below.

TABLE 5

Numbers represent percent of Degradant 1 (w/w).

| Head space, pH | Initial | Post T.S. | 30° C. | 40° C. | 50° C. |
|---|---|---|---|---|---|
| 4% O$_2$, pH 4.2 | 0.002% | 0.004% | 0.003% | 0.005% | 0.009% |
| 6% O$_2$, pH 4.2 | 0.002% | 0.004% | 0.004% | 0.005% | 0.011% |
| 10% O$_2$, pH 4.2 | 0.004% | 0.003% | 0.004% | 0.006% | 0.015% |
| Air, pH 4.6 | 0.003% | 0.003% | 0.008% | 0.015% | 0.033% |
| Air, pH 4.2 | 0.003% | 0.004% | 0.004% | 0.006% | 0.032% |
| Air, pH 3.9 | 0.003% | 0.003% | 0.009% | 0.019% | 0.040% |

TABLE 6

Numbers represent percent of Degradant 2 (w/w).

| Head space, pH | Initial | Post T.S. | 30° C. | 40° C. | 50° C. |
|---|---|---|---|---|---|
| 4% O$_2$, pH 4.2 | 0.003% | 0.006% | 0.008% | 0.010% | 0.017% |
| 6% O$_2$, pH 4.2 | 0.003% | 0.006% | 0.008% | 0.010% | 0.019% |
| 10% O$_2$, pH 4.2 | 0.002% | 0.006% | 0.009% | 0.013% | 0.024% |
| Air, pH 4.6 | 0.002% | 0.005% | 0.012% | 0.018% | 0.043% |
| Air, pH 4.2 | 0.001% | 0.005% | 0.008% | 0.012% | 0.042% |
| Air, pH 3.9 | 0.001% | 0.003% | 0.013% | 0.023% | 0.051% |

What is claimed is:

1. A pharmaceutical composition comprising a pharmaceutically effective amount of (1S,2S)-1-(4-hydroxyphenyl)-2-(4-hydroxy-4-phenylpiperidin-1-yl)-1-propanol or a pharmaceutically acceptable salt thereof and water, wherein said composition contains less than about 2 parts per million of free copper ion and less than about 2 parts per million of free iron ion.

2. A pharmaceutical composition of claim 1, wherein said composition is substantially free of free copper ion and free iron ion.

3. A composition of claim 1, wherein said composition contains less than about 2 parts per million of any free trace metal ion.

4. A pharmaceutical composition of claim 3, wherein said composition is substantially free of any free trace metal ion.

5. A pharmaceutical composition of claims 1–4, further comprising a pharmaceutically acceptable buffer at a concentration effective to maintain the pH of the composition at between about 3.8 to about 5.0.

6. A pharmaceutical composition of claims 1–4, further comprising a pharmaceutically acceptable buffer at a concentration effective to maintain the pH of the composition at between about 4.0 to about 4.5.

7. A pharmaceutical composition of claims 1–4, further comprising a pharmaceutically acceptable buffer at a concentration effective to maintain the pH of the composition at between about 3.8 to about 5.0 wherein the anion of said buffer is selected from acetate, citrate, tartrate, formate and lactate.

8. A pharmaceutical composition of claims 1–4, further comprising a pharmaceutically acceptable buffer at a concentration effective to maintain the pH of the composition at between about 3.8 to about 5.0 wherein the anion of said buffer is lactate.

9. A pharmaceutical composition of claims 1–4, wherein said composition is substantially free of oxygen.

10. A pharmaceutical composition comprising (1S,2S)-1-(4-hydroxyphenyl)-2-(4-hydroxy-4-phenylpiperidin-1-yl)-1-propanol or a pharmaceutically acceptable salt thereof, water and a pharmaceutically acceptable chelating agent at a concentration effective to chelate with trace metal ions present in said composition.

11. A pharmaceutical composition of claim 10 wherein said chelating agent is selected from ethylenediaminetetraacetic acid, citric acid, succinic acid and tartric acid and pharmaceutically acceptable salts thereof.

12. A pharmaceutical composition of claim 10, further comprising a pharmaceutically acceptable buffer at a concentration effective to maintain the pH of the composition at between about 3.8 to about 5.0.

13. A pharmaceutical composition of claim 12, wherein the anion of said buffer is selected from acetate, citrate, tartrate, formate and lactate.

14. A pharmaceutical composition of claim 10, wherein said composition is substantially free of oxygen.

15. A pharmaceutical composition comprising (1S,2S)-1-(4-hydroxyphenyl)-2-(4-hydroxy-4-phenylpiperidin-1-yl)-1-propanol or a pharmaceutically acceptable salt thereof in an aqueous solution, wherein the percent of the degradation product, 4-hydroxybenzaldehyde, is no more than about 0.15 percent of said composition following storage at 50° C. for 12 weeks.

16. A pharmaceutical composition of claim 15, wherein the percent of said degradation product is no more than about 0.07 percent.

17. The pharmaceutical composition of claim 16, wherein the percent of said degradation product is no more than about 0.04 percent.

18. A pharmaceutical composition comprising (1S,2S)-1-(4-hydroxyphenyl)-2-(4-hydroxy-4-phenylpiperidin-1-yl)-1-propanol or a pharmaceutically acceptable salt thereof in an aqueous solution, wherein the percent of the degradation product, 4-hydroxy-4-phenylpiperidine, is no more than about 0.2 percent of said composition following storage at 50° C. for 12 weeks.

19. A pharmaceutical composition of claim 18, wherein the percent of said degradation product is no more than about 0.1 percent.

20. A pharmaceutical composition of claim 19, wherein the percent of said degradation product is no more than about 0.05 percent.

21. A method of preparing a pharmaceutical composition of (1S,2S)-1-(4-hydroxyphenyl)-2-(4-hydroxy-4-phenylpiperidin-1-yl)-1-propanol comprising combining a pharmaceutically effective amount of (1S,2S)-1-(4-hydroxyphenyl)-2-(4-hydroxy-4-phenylpiperidin-1-yl)-1-propanol or a pharmaceutically acceptable salt thereof with a vehicle comprising water wherein said vehicle has been treated with a means to remove trace metal ions.

22. A method of preparing a pharmaceutical composition of (1S,2S)-1-(4-hydroxyphenyl)-2-(4-hydroxy-4-phenylpiperidin-1-yl)-1-propanol comprising:

combining a pharmaceutically effective amount of (1S,2S)-1-(4-hydroxyphenyl)-2-(4-hydroxy-4-phenylpiperidin-1-yl)-1-propanol or a pharmaceutically acceptable salt thereof with a vehicle comprising water to form an aqueous solution; and treating said aqueous solution with a means to remove trace metal ions.

23. A method of treating stroke, spinal cord trauma, traumatic brain injury, multiinfarct dementia, CNS degenerative diseases such as Alzheimer's disease, senile dementia of the Alzheimer's type, Huntington's disease, Parkinson's disease, epilepsy, amyotrophic lateral sclerosis, pain, AIDS dementia, psychotic conditions, drug addictions, migraine, hypoglycemia, anxiolytic conditions, urinary incontinence or an ischemic event arising from CNS surgery, open heart surgery or any procedure during which the function of the cardiovascular system is compromised, in a mammal, comprising administering to a mammal in need of such treatment a pharmaceutical composition of claim 1.

* * * * *